United States Patent [19]

Yoshioka et al.

[11] Patent Number: 4,533,495
[45] Date of Patent: Aug. 6, 1985

[54] METHOD OF PRODUCING 2-AZETIDINONE-1-SULFONIC ACID COMPOUNDS

[75] Inventors: Kouichi Yoshioka, Kyoto; Michihiko Ochiai, Suita, both of Japan

[73] Assignee: Takeda Chemical Industries, Ltd., Osaka, Japan

[21] Appl. No.: 456,075

[22] PCT Filed: Feb. 19, 1982

[86] PCT No.: PCT/JP82/00044

§ 371 Date: Dec. 30, 1982

§ 102(e) Date: Dec. 30, 1982

[51] Int. Cl.$^3$ .............. C07D 205/08; C07D 403/12; C07D 403/06; C07D 401/12

[52] U.S. Cl. ............................ 260/239 A; 260/245.4; 260/330.3; 260/330.9; 260/501.12; 544/238; 544/279; 544/316; 544/319; 544/335; 544/336; 544/359; 544/408; 546/114; 546/122; 546/153; 546/157; 546/172; 546/208; 546/275

[58] Field of Search ............ 260/239 A, 245.4, 330.3, 260/330.9; 546/208, 275, 114, 153, 157, 172, 122; 544/238, 316, 319, 335, 359, 336, 408, 279

[56] References Cited

U.S. PATENT DOCUMENTS 4,159,279 6/1979 Smith et al. ..................... 424/315

FOREIGN PATENT DOCUMENTS 2071650 9/1981 United Kingdom .

OTHER PUBLICATIONS

Imada et al., Nature, 289, 590, (1981).
Sykes et al., Nature, 291, 489, (1981).

European Patent Publication No. 0021678.

*Primary Examiner*—Mark L. Berch
*Attorney, Agent, or Firm*—Wenderoth, Lind & Ponack

[57] ABSTRACT

A compound of the formula:

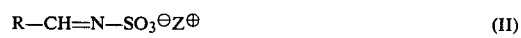

$$R-CH=N-SO_3^{\ominus}Z^{\oplus} \quad (II)$$

[R is an organic residue derived by removal of one hydrogen atom attached to a carbon atom of an organic compound; $Z^{\oplus}$ is a lipophilic quaternary ammonium group], and a method of producing a 2-azetidinone-1-sulfonic acid compound of the formula:

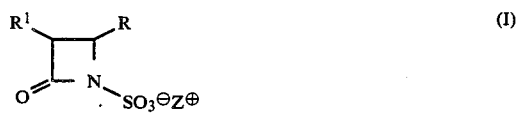

(I)

[R and $Z^{\oplus}$ have the same meanings as respectively defined above; $R^1$ is an acylated or protected amino group or an azide group], being a useful intermediate for the production of antimicrobial agents having excellent antimicrobial and $\beta$-lactamase-inhibitory activities, by reacting a compound (II) with a reactive derivative of a carboxylic acid of the formula:

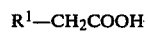

$$R^1-CH_2COOH$$

[$R^1$ is the same meaning as defined above] in the presence of a base.

4 Claims, No Drawings

METHOD OF PRODUCING 2-AZETIDINONE-1-SULFONIC ACID COMPOUNDS

TECHNICAL FIELD

This invention relates in one aspect to a method of producing 2-azetidinone-1-sulfonic acid compounds which are useful intermediates for the production of antimicrobial agents having improved antimicrobial and β-lactamase-inhibitory activities and in another aspect to materials for use in said method.

BACKGROUND TECHNOLOGY

Recently, a new type of β-lactam antibiotic having a sulfo group in 1-position has been found to be recoverable from nature sources and reported [Nature 289, 590 (1981), 291, 489 (1981)]. Syntheses of compounds analogous thereto have also been reported (e.g. Japanese Published unexamined patent application Nos. 164672/1970 and No. 125362/1971). In the latter report is a description of a method for synthesis of 2-azetidinone-1-sulfonic acid compound having a substituent group in 4-position. This method involves a long and complicated series of reaction steps and there has not been developed an expedient synthetic process.

DISCLOSURE OF THE INVENTION

This invention relates to a method of producing an 2-azetidinone-1-sulfonic acid compound of the formula:

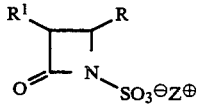
(I)

[R is an organic residue derived by removal of one hydrogen atom attached to a carbon atom of an organic compound; $R^1$ is an acylated or protected amino group or an azide group; $Z^\oplus$ is a lipophilic quaternary ammonium group] and a novel compound used in the above-mentioned method and having the formula:

(II)

[The symbols have the meanings respectively defined above.]

The studies conducted by the present inventors led to the finding that if a compound (II) is reacted with a reactive derivative of a carboxylic acid of the formula:

(III)

[$R^1$ has the same meaning as defined above] in the presence of a base, the desired compound (I) can be produced in good yield and at low cost and that, while some species of the compound (I) thus obtained have excellent antimicrobial activity of their own, the compound (I) generally is a useful intermediate that can be easily transformed into a compound of the formula:

(IV)

[$R^{1\prime}$ is an acylated amino group; $R'$ is an organic residue derived by removal of one hydrogen atom attached to a carbon atom of an organic compound, which may be the same as or different from R] which has excellent antimicrobial and β-lactamase inhibitory activities. This invention has been accomplished on the basis of the above finding.

This invention is, therefore, directed to:

(1) a method of producing an 2-azetidinone-1-sulfonic acid compound (I) characterized by reacting a compound (II) with a reactive derivative of a carboxylic acid (II) in the presence of a base; and (2) a compound (II).

In the foregoing formulas (I), (II) and (III), the symbol R and R' each is an organic residue attached to the 2-azetidinone nucleus at the 4-position through a carbon atom in said organic residue, or to the group: $-CH=N-SO_3^\ominus Z^\oplus$. Such organic residue includes, for example, alkyl, cycloalkyl, alkenyl, alkynyl, cycloalkenyl, aryl, a heterocyclic group, and the like, which may optionally be substituted by one or more substituents. Hereinafter, in this specification, any group which may optionally be substituted will be designated by a superscript asterisk "*". For example, an alkyl which may optionally be substituted will be represented by "alkyl*". In such cases, the number of the substituents is not restricted to one, and some substituted groups may have two to a few substituents which may be the same or different. The alkyl is preferably a straight or branched-chain lower alkyl having 1 to 6 carbon atoms, such as methyl, ethyl, n-propyl, isopropyl, n-butyl, isobutyl, sec-butyl, tert-butyl, n-pentyl, isopentyl, n-hexyl, isohexyl or the like. The cycloalkyl preferably has 3 to 8 carbon atoms and includes, for example, cyclopropyl, cyclobutyl, cyclopentyl, cyclohexyl, cycloheptyl, adamantyl, etc. The alkenyl is preferably a straight or branched-chain lower alkenyl having 2 to 6 carbon atoms such as vinyl, allyl, isopropenyl, 2-methallyl, 2-butenyl, 3-butenyl or the like. The alkynyl is preferably a straight or branched-chain lower alkynyl having 2 to 6 carbon atoms such as ethynyl, 1-propynyl, 2-propynyl or the like. The cycloalkenyl includes, for example, those having 3 to 8 carbon atoms such as 1-cyclopropenyl, 1-cyclobutenyl, 1-cyclopentenyl, 2-cyclopentenyl, 3-cyclopentenyl, 1-cyclohexenyl, 2-cyclohexenyl, 3-cyclohexenyl, 1-cycloheptenyl, 1,4-cyclohexadienyl, etc. Among others, a cycloalkenyl having 4 to 6 carbon atoms is preferred. The aryl includes, for example, phenyl, α-naphthyl, β-naphthyl, biphenyl, anthryl and the like. Of these, phenyl and naphthyl are usually advantageous. The heterocyclic group includes, for example, 5 to 8-membered heterocyclic rings having one to a few hetero-atoms such as nitrogen (inclusive of N-oxide), oxygen and sulfur, as well as fused rings corresponding thereto, which have an available bonding site at a carbon atom thereof. Examples of such heterocyclic group which are usually advantageous include 2- or 3-pyrrolyl, 2- or 3-furyl, 2- or 3-thienyl, 2- or 3-pyrrolidinyl, 2-, 3- or 4-pyridyl, N-oxido-2-, 3- or 4-pyridyl, 2-, 3- or 4-piperidinyl, 2-, 3- or 4-pyranyl, 2-, 3- or 4-thiopyranyl, pyrazinyl, 2-, 4- or 5-thiazolyl, 2-, 4- or 5- oxazolyl, 3-, 4- or 5-isothiazolyl, 3-, 4- or 5-isoxazolyl, 2-, 4- or 5-imidazolyl, 3-, 4- or 5-pyrazolyl, 3- or 4-pyridazinyl, N-oxido-3- or 4-pyridazinyl, 2-, 4- or 5-pyrimidinyl, N-oxido-2-, 4- or 5-pyrimidinyl, piperazinyl, 4- or 5-(1,2,3-thiadiazolyl), 3- or 5-(1,2,4-thiadiazolyl), 1,3,4-thiadiazolyl, 1,2,5-thiadiazolyl, 4- or 5-(1,2,3-oxadiazolyl), 3- or 5-(1,2,4-oxadiazolyl), 1,3,4-oxadiazolyl, 1,2,5-oxadiazolyl, 1,2,3- or 1,2,4-triazolyl, 1H- or 2H-tetrazolyl, pyrido[2,3-d]pyrimidyl, benzopyranyl, 1,8-, 1,5-, 1,6-, 1,7- 2,7- or 2,6-naphthyridyl, quinolyl, thieno[2,3-b]pyridyl and the like. Among others, a 5- or 6-membered heterocyclic ring having one to four hetero-atoms selected from nitrogen and sulfur, such as thienyl, thiazolyl, thiadiazolyl, triazolyl, tetrazolyl or the like is preferred.

Of these groups, the alkyl, alkenyl and alkynyl groups may be substituted with 1 to 3 substituents such as, for example, cycloalkyl*, cycloalkenyl*, aryl*, a heterocyclic group*, alkoxycarbonyl, acyl, oxo, halogen, cyano, hydroxy, alkoxy, aryl*-oxy, acyloxy, carbamoyloxy, hydroxysulfonyloxy, alkylsulfonyloxy, aryl*-sulfonyloxy, nitro, amino, carboxy, aminocarbonyl, alkylthiocarbonyl, mercapto, alkylthio, aminoalkylthio, acylaminoalkylthio, aralkyl*-thio, aryl*thio, heterocycle*-thio, quaternary ammonium* or the like. The substituted alkyl group includes, for example, a group of the formula [A]:

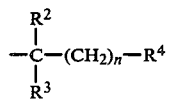

[A]

wherein n is an integer of 0 to 3; $R^2$ and $R^3$ which may be the same or different, stand for hydrogen, alkyl, cycloalkyl*, aralkyl*, aryl*, heterocyclic group*, alkoxycarbonyl or acyl, or $R^2$ and $R^3$ taken together stand for oxo; and $R^4$ is hydrogen, alkyl, cycloalkyl*, aryl*, a heterocyclic group*, halogen, cyano, hydroxy, alkoxy, aryl*-oxy, aralkyl*-oxy, acyloxy, carbamoyloxy, hydroxysulfonyloxy, alkylsulfonyloxy, aryl*-sulfonyloxy, sulfoxy, nitro, amino, azido, carboxy, alkoxycarbonyl, alkoxycarbonylalkyloxy, aminocarbonyl, alkylthiocarbonyl, acyl, mercapto, alkylthio, aminoalkylthio, acylaminoalkylthio, aralkyl*-thio, aryl*-thio, heterocycle*-thio or quaternary ammonium*. In the substituent on the alkyl, alkenyl and alkynyl group, and the group represented by $R^2$, $R^3$ or $R^4$, the alkoxy is preferably a straight or branched-chain lower alkoxy having 1 to 6 carbon atoms such as methoxy, ethoxy, n-propoxy, isopropoxy, n-butoxy, isobutoxy, secbutoxy, tert-butoxy, n-pentyloxy, isopentyloxy, n-hexyloxy, isohexyloxy or the like. Aralkyl includes, for example, benzyl, phenethyl, phenylpropyl, naphthylmethyl, etc. The halogen includes fluorine, chlorine, bromine and iodine. The quaternary ammonium group includes, for example, a group of the formula:

wherein W is hydrogen, methyl, carbamoyl, carboxyl, sulfo or alkoxyl, which may be derived from pyridine derivatives such as pyridine, carbamoyl-substituted pyridine (e.g. nicotinamide, isonicotinamide, etc.), carboxyl-substituted pyridine (e.g. nicotinic acid, isonicotinic acid, etc.), sulfo-substituted pyridine (e.g. pyridine sulfonic acid, etc.); quinolinium, etc. The acyl includes, for example, formyl, alkylcarbonyl, aryl*-carbonyl, aralkyl*-carbonyl, heterocycle*-acetyl, etc. as well as the acyl groups in $R^1$ or $R^{1'}$ mentioned below. Of these, for example, $C_{1-6}$ alkylcarbonyl (e.g. acetyl, propionyl, n-butyryl, isobutyryl, n-pentanoyl, n-hexanoyl, etc.), benzoyl which may be substituted (e.g. benzoyl, 4-hydroxybenzoyl, 4-methoxybenzoyl, etc.), $C_{7-9}$ aralkylcarbonyl which may be substituted (e.g. phenylacetyl, 4-hydroxyphenylacetyl, 4-methoxyphenylacetyl, etc.), 5-membered heterocyclic group containing at least one of oxygen, nitrogen and sulfur, which may be substituted (e.g. 2-thienylcarbonyl, 2-furylcarbonyl, 2-, 4- or 5-thiazolylacetyl, 2- or 3-thienylacetyl, 2- or 3-furylacetyl, 2-amino-4- or 5-thiazolylacetyl, etc.) are preferred. And, the alkyl moiety of alkylsulfonyloxy, alkylthiocarbonyl, alkylthio, aminoalkylthio, acylaminoalkylthio and alkoxycarbonylalkyloxy; the alkoxyl moiety of alkoxycarbonyl and alkoxycarbonylalkyloxy; and the acyl moiety of acyloxy and acylaminoalkylthio have the same meanings as mentioned above.

The substituents which can be present on the cycloalkyl, cycloalkenyl, aralkyl, aryl, heterocyclic and quaternary ammonium groups include, for example, alkyl, alkoxy, alkenyl, aryl, aralkyl, mercapto, alkylthio, arylthio, aralkylthio, alkylsulfonyl, arylsulfonyl, aralkylsulfonyl, hydroxy, oxo, thioxo, halogen, nitro, amino, cyano, carbamoyl, carboxy, acyl, acyloxy, acylamino, hydroxyalkyl, carboxyalkyl, haloalkyl, mono- or dialkylaminoalkyl and the like (wherein the alkyl, alkoxy, alkenyl, aryl, aralkyl, acyl and halogen are those as exemplified above).

When the organic residue R or R' attached to the azetidine ring through a carbon atom therein contains an amino group, said amino group may be substituted or protected, and a carboxyl and a hydroxyl groups, if any, may be likewise protected. The substituents which can be present on the amino group include the acyl in $R^1$ or $R^{1'}$ mentioned below, as well as alkyl, alkoxy, hydroxyalkyl, aralkyl*, aryl*, heterocyclic group*, sulfo, alkylsulfonyl, aralkyl*-sulfonyl, aryl*-sulfonyl, alkoxycarbonyl, aralkyl*-oxycarbonyl, aryl*-oxycarbonyl and the like (wherein the alkyl, alkoxy, aralkyl*, aryl* and heterocyclic group* are those as exemplified above). Optionally the amino group, taken together with such substituent, may form a cyclic amino group such as pyrrolidino, piperidino, morpholino, piperazino or the like. The protective group for amino includes, for example, those exemplified below as the "protective group for amino" for $R^1$. The protective group for carboxyl includes any group which can be conventionally used as a carboxy-protecting group in the fields of β-lactam and other organic chemistry, such as ester residues (e.g., methyl, ethyl, n-propyl, isopropyl, tert-butyl, tert-amyl, benzyl, p-nitrobenzyl, p-methoxybenzyl, benzhydryl, phenacyl, phenyl, p-nitrophenyl, methoxymethyl, ethoxymethyl, benzyloxymethyl, acetoxymethyl, pivaloyloxymethyl, β-methylsulfonylethyl, β-trimethylsilylethyl, methylthiomethyl, trityl, β, β, β-trichloroethyl, β-iodoethyl, trimethylsilyl, dimethylsilyl, acetylmethyl, p-nitrobenzoylmethyl, p-mesylbenzoylmethyl, phthalimidomethyl, propionyloxymethyl, 1,1-dimethylpropyl, 3-methyl-3-butenyl, succinimidomethyl, 3,5-di-tert-butyl-4-hydroxybenzyl, mesylmethyl, benzenesulfonylmethyl, phenylthiomethyl, dimethylaminoethyl, pyridine-1-oxido-2- methyl, methylsulfinylmethyl, bis(p-methoxyphenyl)-methyl, 2-cyano-1,1-dimethylethyl, etc.), silyl, and the like. The protective group for hydroxyl includes any group which can be conventionally used as a hydroxy-protecting group in the fields of β-lactam and other organic chemistry, such as ester residues, e.g., acetyl, chloroacetyl, etc.; esterified carboxyl groups, e.g., β, β, β-trichloroethoxycarbonyl, β-trimethylsilylethoxycarbonyl, etc.; ether residues, e.g., tert-butyl, benzyl, p-nitrobenzyl, trityl, methylthiomethyl, β-methoxyethoxymethyl, etc.; silylether residues, e.g., trimethylsilyl, tert-butyldimethylsilyl, etc.; acetal residues, e.g., 2-tetrahydropyranyl, 4-methoxy-4-tetrahydropyranyl, etc. and the like. The choice of the above-mentioned hydroxy-protecting group is not critical in the present invention, as is the case with the amino- and carboxy-protecting groups.

In the foregoing formulas (I) and (II), $R^1$ is an amino group which may optionally be acylated or protected or an azide group, and in the formula (IV), $R^{1'}$ is an acylated amino group, and the acyl group in the acylated amino group includes any of the conventional acyl groups on the 6- and 7-amino groups of known penicillin derivatives and cephalosporin derivatives, respectively. Examples of the acyl group include a group of the formula:

$$R^5-CO-$$

wherein $R^5$ is a lower alkyl or a heterocyclic* group, a group of the formula:

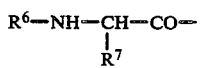
$$R^6-NH-CH-CO-$$
$$\qquad\qquad\quad |$$
$$\qquad\qquad\quad R^7$$

wherein $R^6$ is hydrogen, an amino acid residue, an amino-protective group or a group $R^8-(CH_2)_{n_1}-CO-$ where $R^8$ is a heterocyclic* group and $n_1$ is an integer of 0 to 2, and $R^7$ is a lower alkyl, phenyl*, heterocycle*-carbonylamino or a heterocyclic group, a group of the formula:

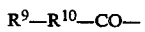
$$R^9-R^{10}-CO-$$

wherein $R^9$ is a group

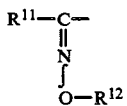
$$R^{11}-C-$$
$$\quad\ \ ||$$
$$\quad\ \ N$$
$$\quad\ \ \backslash$$
$$\quad\ \ \ O-R^{12}$$

where $R^{11}$ is alkyl*, a heterocyclic* group or phenyl* and $R^{12}$ is hydrogen, a lower alkyl, lower alkenyl or a group $-R^{13}-R^{14}$ where $R^{13}$ is a lower alkylene or lower alkenylene and $R^{14}$ is phenyl*, carboxyl or an ester thereof, or mono- or di(lower alkyl)amino, and $R^{10}$ is a direct bond or a group

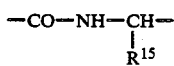
$$-CO-NH-CH-$$
$$\qquad\qquad\quad |$$
$$\qquad\qquad\quad R^{15}$$

where $R^{15}$ is a lower alkyl, phenyl* or thiazolyl*, a group of the formula:

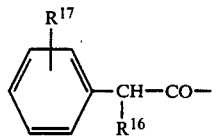

wherein $R^{16}$ is hydroxy, hydroxysulfonyloxy, carboxy, ureido*, sulfamoyl*, sulfo, phenoxyc*arbonyl or formyloxy and $R^{17}$ is hydrogen, a lower alkyl, a lower alkoxy, halogen, nitro or hydroxy, a group of the formula:

$$R^{18}-R^{19}-CH_2-CO-$$

wherein $R^{18}$ is cyano, phenyl*, phenoxy*, a lower alkyl*, alkenylene* or a heterocyclic* group and $R^{19}$ is a direct bond or $-S-$, and the like.

In symbols $R^5$ through $R^{19}$, the alkyl, heterocyclic group, alkoxy and halogen include those exemplified above for R and R'. The amino acid residue includes, for example, glycyl, alanyl, valyl, leucyl, isoleucyl, seryl, threonyl, cysteinyl, cystyl, methionyl, α- or β-aspartyl, α- or γ-glutamyl, lysyl, arginyl, phenylalanyl, phenylglycyl, tyrosyl, histidyl, tryptophanyl, prolyl and the like. The protective group for amino includes those exemplified below as the "protective group for amino". The alkylene as preferably a straight or branched-chain lower alkylene having 1 to 3 carbon atoms and includes, for example, methylene, ethylene, propylene, isopropylene, etc. The alkenylene is preferably a straight or branched-chain lower alkenylene having 2 to 4 carbon atoms such as vinylene, propenylene, or the like. The carboxylic ester includes lower alkyl esters having 1 to 6 carbon atoms in said alkyl moiety such as methyl ester, ethyl ester, propyl ester, n-butyl ester, isobutyl ester, tert-butyl ester, etc. The substituents on the heterocyclic* group, phenyl*, thiazolyl*, phenoxyc*arbonyl and phenoxy* include those substituents on the heterocyclic* group and aryl* described above for R and R'. In addition, the substituent on the thiazolyl* may include, for example, an acylamino having 2 to 4 carbon atoms substituted with alkyl, alkoxy, halogen, hydroxy, amino, or the like, and the substituent on the heterocyclic* group may include, for example, phenyl substituted with alkyl, alkoxy, halogen, nitro, amino, etc. The substituent on the ureido* include, for example, sulfo in the form of salt with a suitable cation such as sodium or potassium; carbamoyl; sulfamoyl; amidino; an alkyl having 1 to 3 carbon atoms; and the like. The substituent on the sulfamoyl* includes, for example, a lower alkyl having 1 to 3 carbon atoms, amidino and the like. The substituent on the lower alkyl* includes, for example, halogen, hydroxy, cyano, tri-fluoromethyl and the like. The substituent on the alkenylene* includes, for example, carboxy, cyano and the like.

The formula

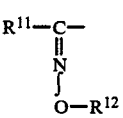

for $R^9$ represents either the syn isomer

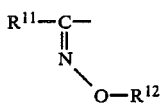

or the anti isomer

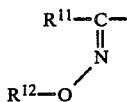

or a mixture thereof.

Especially, in view of the antibiotic activities, a group of the formula:

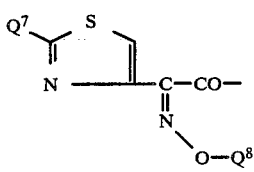

wherein $Q^7$ is amino or a protected amino group, and $Q^8$ is a lower alkyl, a lower alkenyl, a group —CH$_2$COOQ$^9$ or a group

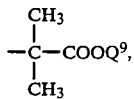

and COOQ$^9$ is carboxyl or an esterified carboxyl group, is more useful as the acyl moiety of the acylated amino group for $R^1$ or $R^{1'}$.

In the above-mentioned acyl groups, examples of the acyl group $R^5$—CO— include 3-(2,6-dichlorophenyl)-5-methylisoxazol-4-yl-carbonyl, 4-ethyl-2,3-dioxo-1-piperazinocarbonyl and the like.

Examples of the acyl group

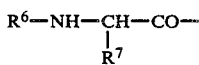

include D-alanyl, benzyl-N$^\alpha$-carbobenzoxy-γ-D-glutamyl-D-alanyl, D-phenylglycyl-D-alanyl, N-carbobenzoxy-D-alanyl, N-carbobenzoxy-D-phenylglycyl, D-alanyl-D-phenylglycyl, γ-D-glutamyl-D-alanyl, 2-(4-ethyl-2,3-dioxo-1-piperazinocarboxamido)-2-phenylacetyl, 2-(4-ethyl-2,3-dioxo-1-piperazinocarboxamido)-2-(4-sulfoxyphenyl)acetyl, N-(4-ethyl-2,3-dioxo-1-piperazinocarbonyl)-D-alanyl, N-(4-ethyl-2,3-dithioxo-1-piperazinocarbonyl)-D-phenylglycyl, 2,2-bis-(4-ethyl-2,3-dioxo-1-piperazinocarboxamido)acetyl, 2-(2-amino-4-thiazolyl)-2-(4-ethyl-2,3-dioxo-1-piperazinocarboxamido)acetyl, 2-(4-hydroxy-6-methyl-nicotinamido)-2-phenylacetyl, 2-(4-hydroxy-6-methyl-nicotinamido)-2-(4-hydroxyphenyl)acetyl, 2-{5,8-dihydro-2-(4-formyl-1-piperazinyl)-5-oxopyrido-[2,3-d]pyrimidine-6-carboxamido}-2-phenylacetyl, 2-(3,5-dioxo-1,2,4-tri-azine-6-carboxamido)-2-(4-hydroxyphenyl)acetyl, 2-(3-furfurideneamino-2-oxoimidazolidine-1-carboxamido)-2-phenylacetyl, 2-(coumarin-3-carboxamido)-2-phenylacetyl, 2-(4-hydroxy-7-methyl-1,8-naphthyridine-3-carboxamido)-2-phenylacetyl, 2-(4-hydroxy-7-trifluoromethylquinoline-3-carboxamido)-2-phenylacetyl, N-[2-(2-amino-4-thiazolyl)acetyl]-D-phenylglycyl, 2-(6bromo-1-ethyl-1,4-dihydro-4-oxo-thieno[2,3-b ]pyridine-3-carboxamido)-2-phenylacetyl, 2-(4-ethyl-2,3-dioxo-1-piperazinocarboxamido)-2-thienylacetyl, 2-(4-n-penthyl-2,3-dioxo-1-piperazinocarboxamido)-2-thienylacetyl, 2-(4-n-octyl-2,3-dioxo-1-piperazinocarboxamido)-2-thienylacetyl, 2-(4-cyclohexyl-2,3-dioxo-1-piperazinocarboxamido)-2-thienylacetyl, 2-[4-(2-phenylethyl)-2,3-dioxo-1-piperzino-carboxamido]-2-thienylacetyl, 2-(3-methylsulfonyl-2-oxoimidazolidine-1-carboxamido)-2-phenylacetyl, 2-(3-furfurideneamino-2-oxoimidazolidine-1-carboxamido)-2-(4-hydroxyphenyl)acetyl, 2-(4-ethyl-2, 3-dioxo-1-piperazinocarboxamido)-2-(4-benzyloxyphenyl)acetyl, 2-(4-ethyl-2,3-dioxo-1-piperazinocarboxamido)-2-(4-methoxyphenyl)acetyl, 2-(8-hydroxy-1,5-naphthyridine-7-carboxamido)-2-phenylacetyl, 2-(2-amino-4-thiazolyl)-2-formamidoacetyl, 2-(2-amino-4-thiazolyl)-2-acetamidoacetyl, and the like.

Examples of the acyl group $R^9$-$R^{10}$—CO— include N-[2-(2-amino-4-thiazolyl)-2-methoxyiminoacetyl]-D-alanyl, N-[2-(2-amino-4-thiazolyl)-2-methoxyiminoacetyl]-D-phenylglycyl, 2-(2-amino-4-thiazolyl)-2-[2-(2-amino-4-thiazolyl)-2-methoxyiminoacetamido]acetyl, 2-(2-chloroacetamido-4-thiazolyl)-2-methoxyiminoacetyl, 2-(2-amino-4-thiazolyl)-2-methoxyiminoacetyl, 2-(2-amino-4-thiazolyl)-2-ethoxyiminoacetyl, 2-(2-amino-4-thiazolyl)-2-propoxyiminoacetyl, 2-(2-amino-4-thiazolyl)-2-butoxyiminoacetyl, 2-(2-amino-4-thiazolyl)-2-benzyloxyiminoacetyl, 2-(2-amino-4-thiazolyl)-2-allyloxyiminoacetyl, 2-(2-amino-4-thiazolyl)-2-[(1-methyl-1-carboxyethyl)oxyimino]acetyl, 2-(2-amino-4-thiazolyl)-2-[(1-methyl-1-methoxycarbonylethyl)oxyimino]acetyl, 2-(2-amino-4-thiazolyl)-2-carboxymethyloxyiminoacetyl, 2-(2-amino-4-thiazolyl)-2-carboxyvinyloxyiminoacetyl, 2-(2-amino-4-thiazolyl)-2-carboxyethyloxyiminoacetyl, 2-(2-amino-4-thiazolyl)-2-methoxycarbonylethyloxyiminoacetyl, 2-(2-amino-5-chloro-4-thiazolyl)-2-methoxyiminoacetyl, 2-(2-amino-5-bromo-4-thiazolyl)-2-methoxyiminoacetyl, 2-(2-amino-4-thiazolyl)-2-oxyiminoacetyl, 2-(2-amino-4-thiazolyl)-2-carboxyethyloxyiminoacetyl, 2-(2-amino-4-thiazolyl)-2-methoxycarbonylethyloxyiminoacetyl, 2-thienyl-2-methoxyiminoacetyl, 2-furyl-2-methoxyiminoacetyl, 2-(1,2,4-thiadiazol-3-yl)-2-methoxyiminoacetyl, 2-(1,2,4-thiadiazol-5-yl)-2-methoxyiminoacetyl, 2-(1,3,4-thiadiazolyl)-2-methoxyiminoacetyl, 2-(4-hydroxyphenyl)-2-methoxyiminoacetyl, 2-phenyl-2-methoxyiminoacetyl, 2-phenyl-2-oxyiminoacetyl, 2-[4-(γ-D-glutamyloxy)phenyl]-2-oxyiminoacetyl, 2-[4-(3-amino-3-carboxypropoxy)phenyl]-2-oxyiminoacetyl, and the like.

Examples of the acyl group

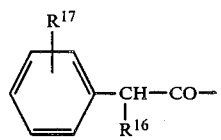

include α-sulfophenylacetyl, α-hydroxyphenylacetyl, α-ureidophenylacetyl, α-sulfoureidophenylacetyl, α-sulfamoylphenylacetyl, α-phenoxycarbonylphenylacetyl, α-(p-tolyloxycarbonyl)phenylacetyl, α-formyloxyphenylacetyl and the like.

Examples of the acyl group $R^{18}$-$R^{19}$—CH$_2$—CO— include cyanoacetyl, phenylacetyl, phenoxyacetyl, trifuloromethylthioacetyl, cyanomethylthioacetyl, 1H-tetrazolyl-1-acetyl, thienylacetyl, 2-(2-amino-4-thiazolyl)acetyl, 4-pyridylthioacetyl, 2-thienylthioacetyl, 3,5-dichloro-1,4-dihydro-4-oxopyridine-1-acetyl, β-carboxyvinylthioacetyl, 2-(2-aminomethylphenyl)acetyl and the like.

The amino, carboxyl and/or hydroxyl group in the above-exemplified acyl groups may be protected by a protective group.

The protective group for amino includes those described below as the "protective group for amino".

The protective groups for carboxyl or hydroxyl include those described above for R and R'.

As the protective group for amino for $R^1$ which may optionally be protected, any of those used for this purpose in the field of β-lactam or peptide synthesis may conveniently be employed. Examples of such amino-protecting group include aromatic acyl groups such as phthaloyl, p-nitrobenzoyl, p-tert-butylbenzoyl, p-tert-butylbenzenesulfonyl, benzenesulfonyl, toluenesulfonyl, etc., aliphatic acyl groups such as formyl, acetyl, propionyl, monochloroacetyl, dichloroacetyl, trichloroacetyl, methanesulfonyl, ethanesulfonyl, trifluoroacetyl, maleyl, succinyl, etc., and esterified carboxyl groups such as methoxycarbonyl, ethoxycarbonyl, t-butoxycarbonyl, isopropoxycarbonyl, 2-cyanoethoxycarbonyl, β, β, β-tri-chloroethoxycarbonyl, β-trimethylsilylethoxycarbonyl, β-methylsulfonylethoxycarbonyl, benzyloxycarbonyl, p-nitrobenzyloxycarbonyl, p-methoxybenzyloxycarbonyl, di-phenyl-methyloxycarbonyl, methoxymethyloxycarbonyl, acetylmethyloxycarbonyl, isobornyloxycarbonyl, phenyloxycarbonyl, etc., as well as non-acyl amino-protecting groups such as trityl, 2-nitrophenylthio, benzylidene, 4-nitrobenzylidene, trialkylsilyl, benzyl, p-nitrobenzyl, proton, etc. The choice of amino-protecting group is not critical in the present invention.

Examples of the lipophilic quaternary ammonium group represented by Z⊕ in the above formulas (I) and (II) are groups represented by the formula

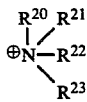

wherein $R^{20}$, $R^{21}$, $R^{22}$ and $R^{23}$ each is a hydrocarbon group which may optionally be substituted and the total number of carbon atoms of hydrocarbon groups $R^{20}$-$R^{23}$ is 10 to 30, preferably 15 to 20. Examples of the optionally substituted hydrocarbon groups represented by $R^{20}$ to $R^{23}$ are such alkyl*, cycloalkyl*, alkenyl*, cycloalkenyl and aryl groups as mentioned for R and R'. Preferable examples of the lipophilic quaternary ammonium group include tetra-n-butylammonium, tetra-n-pentylammonium, tetra-n-hexylammonium, tri-n-octylmethylammonium, di-n-octyldimethylammonium, di-n-decyldimethylammonium, n-hexadecyldimethylammonium and n-tetradecylbenzyldimethylammonium.

According to this invention, a compound (II) is reacted with a reactive derivative of carboxylic acid (III) in the presence of a base to produce 2-azetidinone-1-sulfonic acid (I).

The compound (II) may be either an isolated compound or a reaction mixture obtained from the process of producing the compound. In the latter case, the reaction can be conducted in the reactor used for preparing the compound (II). Usable reactive derivatives of carboxylic acid (III) are, for example, acid halides, acid anhydrides, active amides, active esters and active thioesters. Some specific examples of such reactive derivatives are:

(1) Acid halides:
Acid chlorides and acid bromides are examples.
(2) Acid anhydrides:
Examples are mixed acid anhydrides with monoalkyl carbonates, aliphatic carboxylic acids (e.g. acetic acid, pivalic acid, valeric acid, isovaleric acid, trichloroacetic acid, etc) and aromatic carboxylic acids (e.g. benzoic acid, etc), and symmetric acid anhydrides.
(3) Active amides:
Amides with, for example, pyrazole, imidazole, 4-substituted imidazole, dimethylpyrazole, benzotriazole, etc.
(4) Active esters:
Examples are esters such as methyl ester, ethyl ester, methoxymethyl ester, propargyl ester, 4-nitrophenyl ester, 2,4-dinitrophenyl ester, trichlorophenyl ester, pentachlorophenyl ester, mesylphenyl ester as well as esters with 1-hydroxy-1H-2-pyridone, N-hydroxysuccinimide, or N-hydroxyphthalimide. (5)Active thioesters:
Examples are thioesters with heterocycle-thiols such as 2-pyridylthiol, 2-benzothiazolylthiol and the like.

The above-mentioned reactive derivatives are selected according to the species of carboxylic acid (III).

Examples of the bases usable in the present invention are organic amines, for example, tertiary amines such as aliphatic tertiary amines (e.g. trimethylamine, triethylamine, tripropylamine, tri-n-butylamine, etc), N-methylpiperidine, N-methylpyrrolidine, cyclohexyldimethylamine, N-methylmorpholine and the like, dialkylamines such as di-n-butylamine, diisobutylamine, dicyclohexylamine and the like, aromatic amines such as pyridine, lutidine γ-collidine and the like, 1,8-diazabicyclo[5,4,0]-7-undecene (DBU) and the like, and inorganic amines, for example, alkali metals such as lithium, sodium, potassium, etc., alkaline earth metals, e.g. calcium, magnesium, etc., hydroxides or carbonates of these alkali metals or alkaline earth metals, quaternary ammonium such as tetraethylammonium, tetrabutylammonium and the like.

In the present method, the reactive derivative of carboxylic acid (III) is generally used in an amount of 1 mole per mole of compound (II), but may be used in excess as long as it does not interfere with the reaction. Depending on the species of compounds (II) and (III) and other reaction conditions, the base is used in an amount of 1 to 30 moles, preferably 1 to 10 moles based on each mole of compound (II). The reaction is usually carried out in a solvent. Usable solvents are ethers such as dioxane, tetrahydrofuran, diethyl ether, diisopropyl ether, etc., esters such as ethyl acetate, ethyl formate, etc., halogenated hydrocarbons such as chloroform, dichloromethane, 1,2-di-chloroethane, 1,1,1-trichloroethane, etc., hydrocarbons such as benzene, toluene, n-hexane, etc., amides such as N,N-dimethylformamide, N,N-dimethylacetamide, etc. and nitriles such as acetonitrile. These and other common organic solvents can be used alone or as a mixture. Among the aforesaid bases, those in liquid state serve as well for a solvent. The reaction temperature is not particularly critical as long as the reaction may proceed satisfactorily. However, the reaction is generally conducted at −50° C. to 150° C. and preferably at −30° C. to 80° C. While it depends on the species of starting materials and base, reaction temperature, the species of solvent, etc., the reaction time is generally between tens of minutes and tens of hours and, in some cases, as long as tens of days.

When the resulting product compound (I) has a protective group, it can be deprotected if necessary. Removal of the protective group can be accomplished by a suitable procedure selected from among the known procedures, for example with the use of an acid or a base, with the use of hydrazine, by reductive deprotection, or by a method consisting of iminohalogenation and subsequent iminoetherification followed, if necessary, by hydrolysis. Referring to the deprotection procedure involving an acid, there can be employed inorganic acids, e.g. hydrochloric acid, sulfuric acid, phosphoric acid, etc., organic acids such as formic acid, acetic acid, trifluoroacetic acid, propionic acid, etc., acidic ion exchange resins, etc., although suitable species of acid depend on the species of protective group and other conditions. As for the deprotection procedure involving a base, the base may for example be selected from among inorganic bases such as the hydroxides and carbonates, etc. of alkali metals (e.g. sodium, potassium, etc.) or alkaline earth metals (e.g. calcium, magnesium, etc.), metal alkoxides, organic amines, quaternary ammonium salts and other organic bases, basic ion exchange resins, etc., although suitable species of base depend on the species of protective group and other conditions. If a solvent is employed in the above procedure employing an acid or a base, it is in many cases a hydrophilic organic solvent, water or a mixture thereof.

With regard to the reductive deprotection procedure, while it depends on the species of protective group and other conditions, there may be utilized the process involving the use of a metal such as zinc or a metal compound such as chromium dichloride, chromium acetate or the like and an acid such as an organic or inorganic acid (e.g. acetic acid, propionic acid, hydrochloric acid, etc.), or the process comprising a catalytic reduction reaction in the presence of a metal catalyst. The catalyst that may be employed for this catalytic reduction includes, among others, platinum catalysts such as platinum wire, platinum sponge, platinum black, platinum oxide, colloidal platinum, etc., palladium catalysts such as palladium sponge, palladium black, palladium oxide, palladium-on-barium sulfate, palladium-on-barium carbonate, palladium-on-carbon, palladium-on-silica gel, colloidal palladium, etc. nickel catalysts such as reducing nickel, nickel oxide, Raney nickel, Urushibara nickel, etc. In the reductive procedure involving a metal and an acid, there is employed a metal such as iron or chromium together with an inorganic acid such as hydrochloric acid or an organic acid such as formic acid, acetic acid, propionic acid or the like. These reductive deprotection reactions are generally conducted in a solvent. For catalytic reduction, as an example, there are generally employed such solvents as alcohols, e.g. methanol, ethanol, propanol, isopropanol, etc., ethyl acetate and so on. In the procedure employing a metal and an acid, there are generally employed water, acetone and so on but if the acid is a liquid, it may be used as the solvent as well.

In the procedure employing an acid or a base or in the reductive deprotection procedure, the reaction is generally conducted under cooling, near room temperature or under warming.

The iminohalogenating agent used for removing the protective group by the procedure consisting of iminohalogenation and iminoetherification followed, if necessary, by hydrolysis may for example be phosphorus trichloride, phosphorus pentachloride, phosphorus tribromide, phosphorus oxychloride, thionyl chloride, phosgene or the like. While the reaction temperature is not particularly critical, this reaction is generally conducted at room temperature or under cooling. The iminoetherifying agent which is reacted with the resulting iminohalide may be an alcohol or a metal alkoxide. Examples of said alcohol include alkanols such as methanol, ethanol, propanol, isopropanol, n-butanol, tert-butanol, etc. or compounds corresponding to these alkanols whose alkyl moieties have been substituted by alkoxy groups such as methoxy, ethoxy, propoxy, isopropoxy, butoxy, etc. As examples of said metal alkoxides there may be mentioned alkali metal alkoxides and alkaline earth metal alkoxides such as those derived from said alcohols, such as sodium alkoxides, potassium alkoxides, calcium alkoxides, barium alkoxides, etc.

Further, if the protective group is, for example, an organic carboxylic acid residue which has a functional substituent group such as a free amino, hydroxy, mercapto, carboxy or sulfo group on the carbon atom adjacent to its carbonyl group, it is advantageous to enhance the reactivity of said carbonyl group, prior to removal of the protective group, by a treatment that will add to the adjacent group effect of such substituent group. Taking as an example the case in which a free amino group is the substituent group on the carbon atom adjacent to said carbonyl group, the free amino acid can be converted to a thioureido group before it is acylated. Thus, this and other known procedures for cleavage of peptide linkages can be utilized for removal of the protective group. While the temperature of this reaction is not particularly critical and can be selected according to the species of protective group, deprotecting method employed, etc., it is desirable to conduct the reaction generally under mild conditions, i.e. under cooling, near room temperature or under warming.

In the case of a compound where R and/or $R^1$ is a group having a carboxy group, the derivative of the carboxy group is likely to be converted to a free carboxy group in the course of this reaction. Such cases are also included in the scope of this invention.

The resulting product compound (I) can be isolated and purified by procedures known per se, e.g. concentration, pH adjustment, redistribution, solvent extraction, crystallization, fractional distillation, chromatography, etc. The product compound (I) has substituent group in 3- and 4-positions and, therefore, includes cis- and transisomers. Moreover, since the carbon atoms in 3- and 4-positions are asymmetric carbon atoms, there exist theoretically a total of 4 different stereoisomers. Similarly, stereoisomers exist when the groups represented by R and/or $R^1$ contain an asymmetric carbon atom. If such isomers are produced in the above reaction, they can be individually isolated, if necessary, by conventional procedures such as column chromatography, recrystallization, etc. Moreover, optically active compounds (I) can also be produced by reacting optically active starting compounds (II) in the above manner.

The product compound (I) can be easily converted to a compound having a free 1-sulfo group by treatment with, for example, an acidic ion exchange resin.

Depending on the species of $R^1$, the compound (I) can be easily converted to an 3-amino compound. By way of example, when the 3-position is azido or benzyloxycarbonylamino, it can be reduced to an amino group; when it is α-methyl-p-alkoxycarbonylvinylamino or t-butyloxycarbonylamino, the same can be converted to an amino group by treatment with an acid; when it is phthalimido, it can be converted to an amino group by treatment with a hydrazine compound. The 3-amino compound thus obtained can be acylated by a known procedure to a compound having an acyl group that may for example be one of those acyl groups substituting the 6-amino groups of penicillin compounds or the 7-amino groups of cephalosporin compounds.

Referring to R of product compound (I), this group can be modified to other groups simultaneously or after conversion of the $-SO_3^\ominus Z^\oplus$ group in 1-position to a sulfo group. Thus, for example, when R is acetoxymethyl, methanesulfonyloxymethyl or iodomethyl, it can be converted to a desired other group by reacting (I) with a suitable nucleophilic agent. The nucleophilic agent may for example be an alkylthiol\*, arylthiol\*, heterocyclethiol\* or pyridine compound, and as a result of such reaction, there is obtained a product compound (I) wherein R is a substituted thiomethyl, a quaternary ammonium-methyl\* or the like, as the case may be. The terms alkyl\*, aryl\*, heterocycle\* and quaternary ammonium\* have the same meanings as defined previously. The reaction is desirably conducted in water, a water-miscible solvent such as acetone, acetonitrile, N,N-dimethylformamide or the like, or a mixture of such solvent and water. There are cases in which an alkali carbonate, an alkali phosphate or the like is preferably added to the reaction system. The reaction is generally carried out at a temperature in the range of 20° to 100° C.

The starting compound (II) is a novel compound which was synthesized by the present inventors for the first time. The present inventors found that if sulfamic acid ($H_2NSO_3H$), which was readily available from commercial sources at low costs but due to its strong acidity and sparing solubility in the common organic solvents was thought to be of limited use as it was, was reacted with a quaternary ammonium salt ($Z^\oplus Y^\ominus$: $Z^\oplus$ is as defined previously and $Y^\ominus$ is an anion) and the reaction product was dehydratively condensed with an aldehyde (R—CHO: R is as defined previously), there was unexpectedly obtained a compound (II). Accordingly, the present inventors succeeded in producing this starting material for this invention.

Thus, the compound (II) is produced by reacting sulfamic acid with a quaternary ammonium salt ($Z^\oplus Y^\ominus$) and, then, subjecting the reaction product to dehydrative condensation with an aldehyde (R—CHO). Sulfamic acid is generally used in its free form but it may be used in the form of a salt, e.g. with an alkaline earth metal such as calcium, magnesium, etc. The quaternary ammonium salt is of the formula $Z^\oplus Y^\ominus$ where $Z^\oplus$ is as defined previously and $Y^\ominus$ is an anion. The anion $Y^\ominus$ may for example be $Cl^\ominus$, $Br^\ominus$, $I^\ominus$, $ClO_4^\ominus$ or $HSO_4^\ominus$. Specific examples of said quaternary ammonium salts include the chlorides, bromides, iodides, perchlorates, hydrogen sulfates, etc., of tetra-n-butylammonium, tetra-n-pentylammonium, tetra-n-hexylammonium, tri-n-octylmethylammonium, di-n-octyldimethylammonium, di-n-decyldimethylammonium, n-hexadecylbenzyldimethylammonium, n-tetradecylbenzyldimetylammonium, etc. Sulfamic acid and said quaternary ammonium salt are reacted in approximately equimolar amounts, although the latter may be used in slight excess. Generally, this reaction is preferably conducted in a non-polar solvent which may for example be chloroform, dichloromethane, 1,2-dichloroethane, 1,1,1-trichloroethane, benzene, toluene, ethyl acetate, diisopropyl ether or the like, although chloroform, dichloromethane and 1,2-dichloroethane are preferred.

As an acceptor for the anion $Y^\ominus$ byproduced in the reaction of sulfamic acid and quaternary ammonium salt $Z^\oplus Y^\ominus$, it is preferable to add to the reaction system an equivalent or an excess of a tertiary amine with respect to the sulfamic acid. The tertiary amine may for example be an aliphatic tertiary amine (e.g. triethylamine, tripropylamine, tributylamine), pyridine, N-methylpiperidine, N-methylpyrrolidine, 1,8-diazabicyclo[5,4,0]-7-undencene (DBU) or the like, although triethylamine, which is readily available, is preferred. The reaction temperature may range from $-20°$ C. to $+150°$ C., the preferred range being room temperature to $+60°$ C. The reaction generally goes to completion in a few minutes to several tens of hours.

The reaction product is then subjected to dehydrative condensation with an aldehyde compound R—CHO. In the formula R—CHO for such aldehydes, R is as defined previously. The specific aldehydes employed commonly are alkylaldehydes, cycloalkylaldehydes, alkenylaldehydes, alkynylaldehydes, cycloalkenylaldehydes, arylaldehydes, alkoxycarbonylaldehydes, heterocyclic aldehydes, etc., each of which may have one to several substituent groups. The substituent groups mentioned just above include, among others, alkyl, aryl, alkoxycarbonyl, acyl, oxo, halogen, cyano, hydroxy, alkoxy, acyloxy, carbamoyloxy, nitro, amino, mercapto, alkylthio, aminoalkylthio, acylaminoalkylthio, etc. When the substituent groups are hydroxy, amino or-/and mercapto, they may be protected. The hydrates of said aldehydes and other derivatives equivalent to such aldehydes, e.g., the corresponding semiacetals with lower alkanols can be similarly employed. The aldehyde compound R—CHO is generally used in a stoichiometrically equivalent proportion with respect to sulfamic acid, although it may be used in excess inasmuch the reaction is not adversely affected. The dehydrative condensation with said aldehyde compound R—CHO can be conducted for example by azeotropic distillation with benzene, toluene or the like or using a dehydrating agent such as a molecular sieve, magnesium sulfate, sodium sulfate, potassium chloride, silica gel or the like. This reaction is generally conducted at room temperature or under heating up to 150° C. The reaction time is generally several tens of minutes to tens of hours, although it varies with the reaction procedure, temperature and other conditions. The compound (II) thus obtained can be isolated and purified by the conventional procedure referred to hereinbefore, but it is more advantageous to use the reaction mixture as a material for the next process.

The present invention is illustrated in further detail below with Examples and Reference Examples, but it is to be understood that the examples are solely for the purpose of illustration and not to be construed as limitations of the invention, and that many variations may be resorted to without departing from the spirit and scope of the invention.

In the following Reference Examples and Examples, except specifically described, the elution in column chromatography was carried out with observation of TLC (Thin Layer Chromatography). In the TLC, were employed Merck pre-coated TLC plate 60F$_{254}$, a developing solvent which is the same as the eluent employed in the column chromatography, and UV detector. Fractions containing the desired compound, having spot on TLC plate which turns red to red-purple under heating with spray of ninhydrin when it is sprayed with 48% HBr and then heated to hydrolize, were collected.

BEST MODE FOR WORKING THE INVENTION

EXAMPLE 1

Tetra-n-butylammonium cis-3-phthalimido-4-styryl-2-azetidinone-1-sulfonate 194.2 mg of sulfamic acid, 738.8 mg of tetra-n-butylammonium iodide and 1.0 ml of triethylamine are added to 10 ml of dichloromethane, followed by stirring at room temperature to give a solution. To the solution is added 318.4 mg of trans-cinnamaldehyde and the mixture is concentrated under reduced pressure. To the residue is added 10 ml of benzene and the mixture is refluxed using a Dean-Stark trap, with water being azeotropically removed. After one hour, the benzene is distilled off to give a Schiff's base from tetra-n-butylammonium sulfamate and trans-cinnamaldehyde (tetra-n-butylammonium cinnamylidenesulfamate) as an oil.

IR $\nu_{max}^{neat}$ cm$^{-1}$: 1660, 1620, 1606, 1465, 1230, 1030

NMR (60 MHz, CDCl$_3$) δ: 0.98(12H, t, J=7 Hz, CH$_3$×4), 1.2–1.9(16H, m, CH$_2$CH$_2$×4), 2.9–3.5(8H, m, NCH$_2$×4), 6.5–7.4(2H, m,

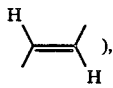

7.35(5H, s, arom H), 8.60(1H, d, J=8 Hz, CH=N)

The above Schiff's base is dissolved in a mixture of 10 ml of dichloromethane and 1.0 ml of triethylamine, and under ice-cooling and stirring in a N$_2$ gas stream a solution of 447 mg of phthalimidoacetyl chloride in dichloromethane (2 ml) is added dropwise over a period of 5 minutes. The mixture is further stirred at room temperature for 10 hours. The reaction mixture is then concentrated under reduced pressure and the residue is purified by column chromatography on silica gel (25 g) using dichloromethane-methanol (10:1) as an eluent. The above procedure gives the above-identified compound as an oil.

IR $\nu_{max}^{neat}$ cm$^{-1}$: 1770, 1720, 1390, 1280, 1250, 1040

NMR(90 MHz, d$_6$-DMSO) δ:0.94(12H, t, J=7 Hz, CH$_3$×4), 1.05–1.80(16H, m, CH$_2$CH$_2$×4), 3.05–3.30(8H, m, NCH$_2$×4), 4.82(1H, dd, J$_1$=6H$_z$, J$_2$=7H$_z$, C$_4$-H), 5.48(1H, d, J=6H$_z$, C$_3$-H), 6.06–6.73(2H, m,

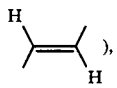

7.22(5H, s, arom H), 7.90(4H, s, arom H).

EXAMPLE 2

Tetra-n-butylammonium cis-3-(1'-methyl-2'-methoxycarbonylvinylamino)-4-styryl-2-azetidinone-1-sulfonate To 50 ml of dichloromethane are added 0.97 g of sulfamic acid, 3.3 g of tetra-n-butylammonium bromide and 2.0 ml of triethylamine and the mixture is stirred at room temperature for an hour. After addition of 1.4 g of transcinnamaldehyde, the dichloromethane is distilled off under atmospheric pressure. To the residue is added 50 ml of benzene and the mixture is distilled slowly at atmospheric pressure (twice) to give a Schiff's base. Separately, 3.17 g of potassium α-methyl-β-methoxycarbonylvinylaminoacetate (Dane salt) is suspended in 60 ml of dichloromethane, and the suspension is cooled to −20° C. ~ −30° C. After addition of 2.1 ml of triethylamine, a solution of 1.44 ml of ethyl chloroformate in 10 ml of dichloromethane is added dropwise. The mixture is stirred at −20° C. ~ −30° C. for 30 minutes, and following dropwise addition of a solution of the above Shiff's base in dichloromethane (20 ml), the mixture is further stirred at room temperature for 3.5 hours. The reaction mixture is filtered with the aid of Celite to remove insolubles, followed by washing with dichloromethane. The filtrate and washings are combined, washed with water and dried over sodium sulfate. The solvent is then distilled off to give the above-identified compound as an oil, yielding 5.7 g.

IR $\nu_{max}^{neat}$ cm$^{-1}$: 3450, 2950, 1760, 1260, 1050.

EXAMPLE 3

Tri-n-octylmethylammonium cis-3-phthalimido-4-styryl-2-azetidinone-1-sulfonate

The procedure of Example 1 is followed but using 97.1 mg of sulfamic acid, 400 mg of tri-n-octylmethylammonium chloride, 0.5 ml of triethylamine and 200 mg of trans-cinnamaldehyde to give the above-identified compound as an oil, yielding 62.5 mg.

IR $\nu_{max}^{neat}$ cm$^{-1}$: 1760, 1710, 1460, 1380, 1260, 1240, 1040.

REFERENCE EXAMPLE 1 cis-3-Amino-4-styryl-2-azetidinone-1-sulfonic acid

In a mixture of 20 ml of ethyl acetate and 10 ml of water is dissolved 1.0 g of tetra-n-butylammonium cis-3-(1'-methyl-2'-methosycarbonylvinylamino)-4-styryl-2azetidinone-1-sulfonate and, following addition of 0.15 ml of phosphoric acid, the mixture is stirred at room temperature for 2 hours. Upon completion of the reaction, the aqueous layer is separated, while the organic layer is extracted twice with 10 ml portions of water. The aqueous layers are combined, washed with ethyl acetate, and adjusted to pH 7.5 with aqueous sodium hydrogen carbonate. The solution is extracted twice with dichloromethane and dried. The dichloromethane is then distilled off to give 330 mg of tetra-n-butylammonium cis-3-amino-4-styryl-2-azetidinone-1-sulfonate. This product is dissolved in 20 ml of methanol and stirred with 3 ml of Dowex 50W (H+-form, Dow Chemical) at room temperature for 30 minutes. The ion exchange resin is filtered off, and the filtrate is washed with methanol. The filtrate and washings are combined and concentrated to dryness to give the above-identified compound as a white powder, yielding 95 mg.

IR $\nu_{max}^{KBr}$ cm$^{-1}$: 3450, 3000, 1770, 1280, 1240, 1045.

REFERENCE EXAMPLE 2 cis-3-Amino-4-styryl-2-azetidinone-1-sulfonic acid

In 10 ml of dichloromethane is dissolved 667 mg of tetra-n-butylammonium cis-3-phthalimido-4-styryl-2-azetidinone-1-sulfonate and, following dropwise addition of 0.1 ml of methylhydrazine, the mixture is stirred at room temperature for 24 hours. The reaction mixture is shaken with water and the dichloromethane layer which separates out is concentrated. To the concentrate is added ethyl acetate and the mixture is extracted with dilute hydrochloric acid. The aqueous layer is made neutral with dilute aqueous sodium hydroxide, extracted with dichloromethane and dried. Removal of the dichloromethane by distillation gives 150 mg of tetra-n-butyl-ammonium cis-3-amino-4-styryl-2-azetidinone-1-sulfonate. This product is then treated with an ion exchange resin in the same manner as Reference Example 1 to give 50 mg of the above-identified compound. The IR spectrum of this product is identical with that of the product obtained in Reference Example 1.

REFERENCE EXAMPLE 3

Sodium cis-3-[2-(2-aminothiazol-4-yl)-(Z)-2-methoxyiminoacetamido]-4-trans-styryl-2-azetidinone-1-sulfonate In 10 ml of N,N-dimethylformamide is dissolved 188 mg of cis-3-amino-4-styryl-2-azetidinone-1-sulfonic acid as obtained in Reference Example 1. Under ice-cooling and stirring, 194 mg of 2-(2-chloroacetamidothiazol-4-yl)-(Z)-2-methoxyiminoacetic acid, 110 mg of N-hydroxybenzotriazole monohydrate and 150 mg of dicyclohexylcarbodiimide are added, and the mixture is stirred at room temperature for 20 hours. To the reaction mixture is added 20 ml of water and the insolubles are filtered off. To the filtrate is added 400 mg of sodium N-methyldithiocarbamate and the mixture is stirred at room temperature for 1.5 hours. The reaction mixture is passed through a column of Amberlite XAD-II (Rohm & Haas), using 5% alcohol as an eluent. The fractions containing the desired product are lyophilized to give the above-identified compound as a powder, yielding 86 mg.

Elemental analysis: Calcd. for $C_{17}H_{16}N_5Na_1O_6S_2.2.5H_2O$: C, 39.38; H, 4.08; N, 13.51. Found: C, 39.29; H, 4.03; N, 13.54.

Industrial Utility

The method of this invention in which the novel compound (II) is used as a starting material provides an intermediate compound (I), which is of value for the synthesis of the compound (IV) having excellent antibacterial and β-lactamase-inhibitory activities, in a single step and at low cost. Therefore, the method is of value in the commercial production of compound (I).

We claim:

1. A method of producing a compound of the formula:

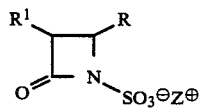

wherein R is
(1) a group of the formula:

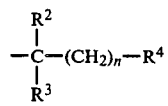

wherein n is an integer of 0 to 3; $R^2$ and $R^3$ which may be the same or different, stand for hydrogen, alkyl, cycloalkyl*, aralkyl*, aryl*, heterocyclic* group, alkoxycarbonyl or acyl, or $R^2$ and $R^3$ taken together stand for oxo; and $R^4$ is hydrogen, alkyl, cycloalkyl*, aryl*, a heterocyclic* group, halogen, cyano, hydroxy, alkoxy, aryl*-oxy, aralkyl*-oxy, acyloxy, carbamoyloxy, hydroxysulfonyloxy, alkylsulfonyloxy, aryl*-sulfonyloxy, sulfoxy, nitro, amino, azido, carboxy, alkoxycarbonyl, alkoxycarbonylalkyloxy, aminocarbonyl, alkylthiocarbonyl, acyl, mercapto, alkylthio, aminoalkylthio, acylaminoalkylthio, aralkyl*-thio, aryl*-thio, or heterocyclic*-thio [or quaternary ammonium*], (2) unsubstituted or substituted alkenyl or alkynyl, the substituent being cycloalkyl*, cycloalkenyl*, aryl*, a heterocyclic* group, alkoxycarbonyl, acyl, oxo, halogen, cyano, hydroxy, alkoxy, aryl*-oxy, acyloxy, carbamoyloxy, hydroxysulfonyloxy, alkylsulfonyloxy, aryl*-sulfonyloxy, nitro, amino, carboxy, aminocarbonyl, alkylthiocarbonyl, mercapto, alkylthio, aminoalkylthio, acylaminoalkylthio, aralkyl*-thio, aryl*-thio, or heterocyclic*-thio [or quaternary ammonium*], or (3) unsubstituted or substituted cycloalkyl, cycloalkenyl, aryl or a heterocyclic group, the substituent being alkyl, alkoxy, alkenyl, aryl, aralkyl, mercapto, alkylthio, arylthio, aralkylthio, alkylsulfonyl, arylsulfonyl, aralkylsulfonyl, hydroxy, oxo, thioxo, halogen, nitro, amino, cyano, carbamoyl, carboxy, acyl, acyloxy, acylamino, hydroxyalkyl, carboxyalkyl, haloalkyl or mono- or di-alkylaminoalkyl, and in the above groups (1) to (3), (a) the heterocyclic group is 2- or 3-pyrrolyl, 2- or 3-furyl, 2- or 3-thienyl, 2- or 3-pyrrolidinyl, 2-, 3- or 4-pyridyl, N-oxido-2-, 3- or 4-pyridyl, 2-, 2-, 3- or 4-piperidinyl, 2, 3- or 4-pyranyl, 2-, 3- or 4-thiopyranyl, pyrazinyl, 2-, 4- or 5-thiazolyl, 2-, 4- or 5-oxazolyl, 3-, 4- or 5-isothiazolyl, 3-, 4- or 5-isoxazolyl, 2-, 4- or 5-imidazolyl, 3-, 4- or 5-pyrazolyl, 3- or 4-pyridazinyl, N-oxido-3- or 4-pyridazinyl, 2-, 4- or 5-pyrimidinyl, N-oxido-2-, 4- or 5-pyrimidinyl, piperazinyl, 4- or 5-(1,2,3-thiadiazolyl), 3- or 5-(1,2,4-thiadiazolyl), 1,3,4-thiadiazolyl, 1,2,5-thiadiazolyl, 4- or 5-(1,2,3-oxadiazolyl), 3- or 5-(1,2,4-oxadiazolyl), 1,3,4-oxadiazolyl, 1,2,5-oxadiazolyl, 1,2,3- or 1,2,4-triazolyl, 1H- or 2H-tetrazolyl, pyrido [2,3-d]pyrimidyl, benzopyranyl, 1,8-, 1,5-, 1,6-, 1,7-2,7- or 2,6-naphtyhridyl, quinolyl or thieno [2,3-b]pyridyl, (b) the acyl group and the acyl moiety of the acyloxy, acylaminoalkylthio or acylamino is $C_{1-6}$ alkylcarbonyl, benzoyl, 4-hydroxybenzoyl, 4-methoxybenzoyl, phenylacetyl, 4-hydroxyphenylacetyl, 4-methoxyphenylacetyl, 2-thienylcarbonyl, 2-furylcarbonyl, 2-, 4- or 5-thiazolylacetyl, 2- or 3-thienylacetyl, 2- or 3-furylacetyl or 2-amino-4- or 5-thiazolylacetyl, and (c) the cycloalkyl, aralkyl, aryl, heterocyclic and cycloalkenyl group with subscript asterisk "*" may be substituted with the substituent as defined above in (3), $R^1$ is (1)' an amino, (2)' an acylated amino group wherein the acyl moiety is (i) a group of the formula:

$$R^5-CO-$$

wherein $R^5$ is alkyl other than $C_{1-5}$ alkyl—$CH_2$— or a heterocyclic* group, (ii) a group of the formula:

$$R^6-NH-\underset{R^7}{CH}-CO-$$

wherein $R^6$ is hydrogen, an amino acid residue, an amino-protective group or a group $R^8-(CH_2)_{n1}-CO-$ where $R^8$ is a heterocyclic* group and $n_1$ is an integer of 0 to 2, and $R^7$ is an alkyl, phenyl*, heterocyclic*-carbonylamino or a heterocyclic group, (iii) a group of the formula:

$$R^9-R^{10}-CO-$$

wherein $R^9$ is a group $$R^{11}-\underset{\underset{O-R^{12}}{\overset{\|}{N}}}{C}-$$

where $R^{11}$ is alkyl*, a heterocyclic* group or phenyl* and $R^{12}$ is hydrogen, an alkyl, alkenyl or a group —$R^{13}$—$R^{14}$ where $R^{13}$ is an alkylene or alkenylene and $R^{14}$ is phenyl*, carboxyl or an ester thereof, or mono- or di- alkylamino, and $R^{10}$ is a direct bond or a group $$-CO-NH-\underset{R^{15}}{CH}-$$

where $R^{15}$ is an alkyl, phenyl* or thiazolyl*, (iv) a group of the formula:

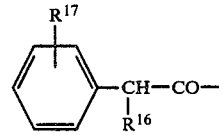

wherein $R^{16}$ is hydroxy, hydroxysulfonyloxy, carboxy, ureido*, sulfamoyl*, sulfo, phenoxycarbonyl* or formyloxy and $R^{17}$ is hydrogen, an alkyl, an alkoxy, halogen, nitro or hydroxy, or (v) a group of the formula:

$$R^{18}-R^{19}-CH_2-CO-$$

wherein $R^{18}$ is cyano, phenyl*, phenoxy*, an alkyl*, alkenyl* or a heterocyclic* group and $R^{19}$ is a direct bond or —S—, and in the above groups (i) to (v), (a)' the heterocyclic group is as defined above in the group R, (b)' the amino acid residue is glycyl, alanyl, valyl, leucyl, isoleucyl, seryl, theonyl, cysteinyl, cystyl, methionyl, α- or β-aspartyl, α- or τ-glutamyl, lysyl, arginyl, phenylalanyl, phenylglycyl, tyrosyl, histidyl or tryptophanyl, (c)' the amino-protective group in R is phthaloyl, p-nitrobenzoyl, p-tert-butylbenzoyl, p-tert-butylbenzenesulfonyl, benzenesulfonyl, toluenesulfonyl, formyl, acetyl, propionyl, monochloroacetyl, dichloroacetyl, trichloroacetyl, methanesulfonyl, ethanesulfonyl, trifluoroacetyl, maleyl succinyl, methoxycarbonyl, ethoxycarbonyl, t-butoxycarbonyl, isopropoxycarbonyl, 2-cyanoethoxycarbonyl, β, β, β, -tri-chloroethoxycarbonyl, β-trimethylsilylethoxycarbonyl, β-methylsulfonylethoxycarbonyl, benzyloxycarbonyl, p-nitrobenzyloxycarbonyl, p-methoxybenzyloxycarbonyl, diphenylmethyloxycarbonyl, methoxymethyloxycarbonyl, acetylmethyloxycarbonyl, isobornyloxycarbonyl, phenyloxycarbonyl, trityl, 2-nitrophenylthio, benzylidene, 4-nitrobenzylidene, trialkylsilyl, benzyl or p-nitrobenzyl, (d)' the alkyl group with a superscript asterisk "*" may be substituted with halogen, hydroxy, cyano or tri-fluoromethyl, (e)' the ester of carboxyl in $R^{14}$ is an alkyl ester having 1 to 6 carbon atoms, (f)' the ureido with a superscript asterisk "*" may be substituted sulfo in the form of salt with sodium or potassium; carbamoyl; sulfamoyl; amidino; or an alkyl having 1 to 3 carbon atoms, (g)' the sulfamoyl with a superscript asterisk "*" may be substituted with an alkyl having 1 to 3 carbon atoms or amidino, (h)' the alkenyl with a superscript asterisk "*" may be substituted with carboxy or cyano, and (i)' the heterocyclic, phenyl, thiazolyl, phenoxycarbonyl and phenoxy with a superscript asterisk "*" may be substituted with the substituent as defined above in (3)

(3)' amino protected with phthaloyl, p-nitrobenzoyl, p-tertbutylbenzoyl, p-tert-butylbenzenesulfonyl, benzenesulfonyl, toluenesulfonyl, formyl, monochloroacetyl, dichloroacetyl, trichloroacetyl, methanesulfonyl, ethanesulfonyl, trifluoro-acetyl, maleyl, succinyl, methoxycarbonyl, ethoxycarbonyl, t-butoxycarbonyl, isopropoxycarbonyl, 2-cyanoethoxycarbonyl, β, β, β-tri-chloroethoxycarbonyl, β-trimethylsilylethoxycarbonyl, β-methylsulfonylethoxycarbonyl, benzyloxycarbonyl, p-nitrobenzyloxycarbonyl, p-methoxybenzyloxycarbonyl, di-phenylmethyloxycarbonyl, methoxymethyloxycarbonyl, acetylmethyloxycarbonyl, isobornyloxycarbonyl, pnenyloxy-carbonyl, trityl, 2-nitrophenylthio, benzylidene, 4-nitrobenzylidene, trialkylsilyl, benzyl or p-nitrobenzyl, or (4)' an azide group, and in the above (1)–(3) and (2)', the amino, carboxyl and hydroxyl group may be protected; the alkyl is $C_{1-6}$ alkyl; the cycloalkyl is $C_{3-8}$ cycloalkyl; the alkenyl is $C_{2-6}$ alkenyl; the alkynyl is $C_{2-6}$ alkynyl; the cycloalkenyl is $C_{3-8}$ cycloalkenyl; the aryl is phenyl, α-naphthyl, β-naphthyl, biphenyl or anthryl; the alkoxy is $C_{1-6}$ alkoxy; the aralkyl is benzyl, phenethyl, phenylpropyl or naphthylmethyl; the alkylene is $C_{1-3}$ alkylene; and the alkenylene is $C_{2-4}$ alkenylene, and $Z^{\oplus}$ is a group of the formula:

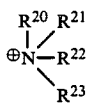

wherein $R^{20}$, $R^{21}$, $R^{22}$ and $R^{23}$ each is an alkyl*, cycloalkyl*, alkenyl*, cycloalkenyl or aryl as defined above in the groups R and $R^1$ and the total number of carbon atoms of $R^{20}$–$R^{23}$ is 10 to 30, characterized by reacting a compound of the formula:

wherein the symbols have the same meanings as respectively defined above, with (1) an acid halide, (2) an acid anhydride, (3) an amide with pyrazole, imidazole, 4-substituted imidazole, dimethylpyrazole or benzotriazole, (4) an ester from the group of methyl ester, ethyl ester, methoxymethyl ester, propargyl ester, 4-nitrophenyl ester, 2,4-dinitrophenylester, trichlorophenyl ester, pentachlorophenyl ester, mesylphenyl ester and esters with 1-hydroxy-1H-2-pyridone, N-hydroxy-succinamide or N-hydroxyphthalimide or (5) a thioester with 2-pyridylthiol or 2-bensothiazolylthiol of a carboxylic acid of the formula:

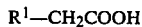

wherein $R^1$ has the same meaning as defined above, in the presence of a base.

2. A method according to claim 1, wherein tetra-n-butylammonium cis-3-phthalimido-4-styryl-2-azetidinone-1-sulfonate is produced.

3. A method of producing tetra-n-butylammonium cis-3-(1'-methyl-2'-methoxycarbonylvinylamino)-4-styryl-2-azetidinone-1-sulfonate characterized by reacting tetra-n-butylammonium cinnamylidenesulfamate with α-methyl-β-methoxycarbonyvinylaminoacetic ethoxycarboxylic anhydride in the presence of triethylamine.

4. A method according to claim 1, wherein tri-n-octylmethylammonium cis-3-phthalimido-4-styryl-2-azetidinone-sulfonate is produced.

* * * * *

UNITED STATES PATENT AND TRADEMARK OFFICE
CERTIFICATE OF CORRECTION

PATENT NO. : 4,533,495  Page 1 of 2
DATED : August 6, 1985
INVENTOR(S) : KOUICHI YOSHIOKA and MICHIHIKO OCHIAI It is certified that error appears in the above-identified patent and that said Letters Patent is hereby corrected as shown below:

Column 18, line 59, change "1,7-2,7-" to --1,7-,2,7- --;

Column 18, line 59, change "naphtyhridyl" to --naphthyridyl--.

Column 19, line 2, change "subscript asterish" to --superscript asterisk--.

Column 20, line 10, change "R" to --$R^6$--;

Column 20, line 35, after "substituted" insert --with--;

Column 20, line 61, change "pnenyloxy-carbonyl" to read --phenyloxy-carbonyl--.

Column 21, line 20, correct the formula to read as follows:

--  --.

UNITED STATES PATENT AND TRADEMARK OFFICE
CERTIFICATE OF CORRECTION

PATENT NO. : 4,533,495

DATED : August 6, 1985

INVENTOR(S) : KOUICHI YOSHIOKA and MICHIHIKO OCHIAI

It is certified that error appears in the above-identified patent and that said Letters Patent is hereby corrected as shown below:

Column 22, line 20, change "methoxycarbonyvinylaminoacetic" to --methoxycarbonylvinylaminoacetic--.

Signed and Sealed this

Fourth Day of February 1986

[SEAL]

Attest:

DONALD J. QUIGG

Attesting Officer

Commissioner of Patents and Trademarks